United States Patent
Jhutty et al.

(10) Patent No.: US 7,661,289 B1
(45) Date of Patent: Feb. 16, 2010

(54) METHOD FOR CALIBRATING AN ACOUSTIC DROPLET DISPENSING APPARATUS

(75) Inventors: Tarlochan S. Jhutty, Saratoga, CA (US); Humphrey W. Chow, Cupertino, CA (US); Kevin Thompson, Fremont, CA (US)

(73) Assignee: EDC Biosystems, Inc., Milpitas, CA (US)

( * ) Notice: Subject to any disclaimer, the term of this patent is extended or adjusted under 35 U.S.C. 154(b) by 292 days.

(21) Appl. No.: 11/897,612

(22) Filed: Aug. 31, 2007

(51) Int. Cl.
*G01N 35/08* (2006.01)
(52) U.S. Cl. .......................... 73/1.02; 73/1.31
(58) Field of Classification Search .................. 347/19; 73/1.02, 1.05, 1.16, 1, 26, 31, 1.67, 1.69, 73/1.74, 53.04, 504.06; 702/100
See application file for complete search history.

(56) References Cited

U.S. PATENT DOCUMENTS

| | | | |
|---|---|---|---|
| 6,612,149 B2 * | 9/2003 | Wang et al. ................... | 73/1.02 |
| 6,719,449 B1 | 4/2004 | Laugharn, Jr. et al. | |
| 7,338,802 B2 * | 3/2008 | Frischauf et al. ............... | 436/8 |
| 2009/0007625 A1 * | 1/2009 | Ao et al. ....................... | 73/1.31 |

OTHER PUBLICATIONS

Jean Shieh, Richard N. Ellson and Joseph Olechno, The Effects of Small Molecule and Protein Solutes on Acoustic Drop Ejection, Journal of the Association for Laboratory Automation (JALA), Aug. 2006, pp. 227-232.

Brent W. Segelke et al., Combinatorial Screening for Protein Crystallization: Advances in Instrumentation for Automated Combinatorial Crystallization Screening, Innovadyne Technologies, Inc., copyright 2006, downloaded May 11, 2007, www.innovadyne.com/appnote_xtal_LLNL.html.

* cited by examiner

*Primary Examiner*—Lamson D Nguyen
(74) *Attorney, Agent, or Firm*—Donald J. Pagel (57) ABSTRACT

The present invention comprises a method for calibrating a droplet dispensing apparatus using acoustic energy to dispense a plurality of droplet sets of a liquid from a source container into a plurality of target containers, with each droplet set being comprised of one or more individual droplets of the liquid, and with a liquid level of the liquid in the source container being measured before each of the droplet sets are dispensed. The average droplet volume for the individual droplets in each of the droplet sets is then calculated by detecting the presence of an indicator, such as a fluorescent chemical. Once the average droplet volume has been calculated, it is determined if the average droplet volume for each droplet set is acceptable or not acceptable. Where the average droplet volume is determined to be not acceptable, an existing droplet dispensing parameter is changed to a new droplet dispensing parameter that will cause the average droplet volume for that droplet set to change. A burst curve is then generated that will cause the new droplet dispensing parameter for each droplet set to be used if a subsequent plurality of droplet sets are dispensed.

11 Claims, 5 Drawing Sheets

METHOD FOR CALIBRATING AN ACOUSTIC DROPLET DISPENSING APPARATUS

BACKGROUND OF THE INVENTION

1. Technical Field

The present invention relates to a method for calibrating an acoustic droplet dispensing apparatus, and more particularly to a method having a step in which the volume of a droplet is correlated to the liquid level of the source liquid.

2. Background Information

Figure 1:
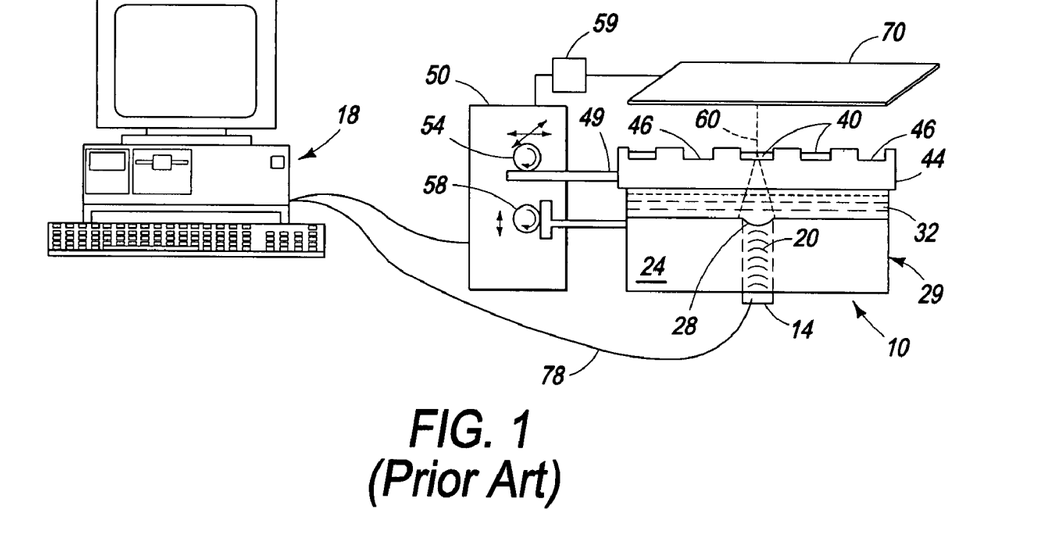
FIG. 1 is a schematic diagram of an acoustic droplet dispensing apparatus of the prior art.

FIG. 1 illustrates an acoustic droplet dispensing apparatus 10 known in the prior art. Apparatuses of this type are capable of dispensing droplets of liquids having volumes as small as approximately one hundred picoliters, and are particularly useful in the biotechnology and biopharmaceutical fields. A representative acoustic droplet dispensing apparatus is described in U.S. Pat. No. 6,863,362 which is incorporated herein by reference.

In the apparatus 10, an acoustic wave emitter 14 (such as a piezoelectric crystal) is in electrical communication with a computer 18. During operation the acoustic wave emitter 14 generates an acoustic wave or beam 20 that can be propagated through an optional wave channel 24. The acoustic wave can be focused by a lens 28 prior to propagating through a coupling medium 32 to optimize the energy of the acoustic wave or beam 20 upon the liquid/air interface (free surface) of a source liquid 40. The assembly comprised of the acoustic wave emitter 14, the wave channel 24 and the lens 28 is referred to as an acoustic emitter assembly 29. The acoustic wave 20 is propagated through the coupling medium 32 after which the wave is transmitted through a source liquid containment structure 44 where the wave comes to focus at or near the surface of the pool of source liquid 40, thereby causing a droplet 60 of the source liquid 40 to be dispensed from the surface of the pool.

Examples of source liquid containment structures 44 include single and multi-well wellplates commonly used in molecular biology applications, capillaries (e.g., capillary arrays), and the like. However, other containers or structures may be used to hold the liquid 40 to be dispensed or ejected. A typical wellplate comprises a matrix (rows and columns) of individual wells 46. Typical commercially available wellplates have 96, 384, 1536 or 3456 individual wells. The source liquid 40 may be contained in some or all of these wells 46 and the composition of the source liquid in individual wells may differ from well to well (i.e. there can be multiple source liquids 40). Furthermore, the volume of source liquid in the individual wells may differ from well to well. The volume of source liquid in an individual well is derived from the liquid level and well geometry.

Optimally, in order to dispense one or more droplets from one of the individual wells 46, the well 46 must be positioned over the acoustic wave emitter 14. To accomplish this, the source fluid containment structure 44 is detachably affixed to a gripper 49. The gripper 49 is controlled by an actuator mechanism 50 which contains a horizontal actuator 54 for moving the containment structure 44 in the horizontal (x and y) directions. A vertical actuator 58 moves the acoustic wave emitter 14 and wave channel 24 in the vertical (z) direction. The actuator 50 is typically in communication with computer 18 which controls the movement of the containment structure 44 to select a source liquid 40 or to adjust focusing of the acoustic wave or beam 20 at or near the surface of the source liquid 40. The computer may have implemented thereon various algorithms to adjust the focal position and energy of the acoustic wave emitter as well as control and manage the location of the acoustic wave emitter relative to a particular source fluid present in or on a source fluid containment structure.

Figure 2:
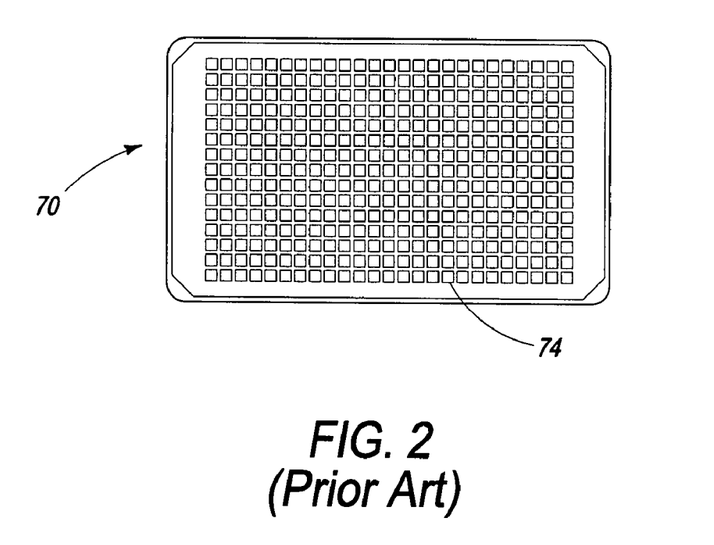
FIG. 2 is a partial isometric view of a wellplate of the prior art.

Accordingly, the apparatus 10 may be used to cause one or more droplets 60 of the source liquid 40 to be dispensed from the containment structure 44 and towards a target substrate 70, as is described in U.S. Pat. No. 6,863,362. The target substrate 70 may be a multi-well wellplate similar to the source fluid containment structure 44, or may be some other type of medium. Generally, one or more horizontal actuators 59 are provided for moving the target substrate 70 in the horizontal (x and y) directions. A typical wellplate that could be used as the target substrate 70 may have 96, 384, 1536 or 3456 individual target wells 74, or some other number of target wells. FIG. 2 illustrates the target wells 74 in a wellplate used as the target substrate 70.

In a preferred embodiment, a piezoelectric transducer is employed as an acoustic wave emitter 14. In one embodiment, a piezoelectric transducer comprises a flat thin piezoelectric element, which is constructed between a pair of thin film electrode plates. As is understood by those of skill in the art, when a high frequency and appropriate magnitude voltage is applied across the thin film electrode plates of a piezoelectric transducer, radio frequency energy will cause the piezoelectric element to be excited into a thickness mode oscillation. The resultant oscillation of the piezoelectric element generates a slightly diverging acoustic beam of acoustic waves. By directing the wave or beam onto an appropriate lens having a defined radius of curvature (e.g., a spherical lens, or the like), the acoustic beam can be brought to focus at a desired point.

In one embodiment, a computer sends an analog voltage pulse to the piezoelectric transducer by an electrical wire 78. The electronics can control the magnitude and duration of the analog voltage pulses, and also the frequency at which the pulses are sent to the piezoelectric transducer. Each voltage pulse causes the generation of an acoustic wave from the piezoelectric transducer, which in turn is propagated through a coupling medium and into or through the source fluid thereby impinging on the surface of the source fluid.

A problem that is encountered in using acoustic droplet dispensing systems, such as the apparatus 10, is that it is difficult to precisely control the volume of the droplets dispensed from the apparatus. In large part, this is because many parameters associated with the source liquid, such as chemical composition, viscosity, temperature, speed of sound in the liquid, etc., affect the size (volume) of the droplet. Furthermore, the liquid level of the source liquid in the well 46 also affects the size (volume) of the droplet. Additionally, other factors, such as the geometry of the source well (e.g. well shape, well bottom thickness, etc.) or the manufacturing variability of the acoustic emitter assembly 29, can influence the size of the droplet. Therefore, what is needed is a technique for calibrating acoustic droplet dispensing systems so that uniform droplet volume can be achieved.

SUMMARY OF THE PRESENT INVENTION

Briefly, the present invention comprises a method for calibrating a droplet dispensing apparatus that uses acoustic energy to dispense a plurality of droplet sets of a liquid from a source container into a plurality of target containers, with each droplet set being comprised of one or more individual droplets of the liquid, and with a liquid level of the liquid in the source container being measured before each of the droplet sets are dispensed. The average droplet volume for the individual droplets in each of the droplet sets is then calculated. Typically, this is done by detecting the presence of an indicator, such as a fluorescent chemical. However, other indicators such as luminescent materials, pigmented materials, scented materials, radioactive materials, reactive materials or inhibiting materials could be used.

Once the average droplet volume has been calculated, it is determined if the average droplet volume for each droplet set is acceptable or not acceptable. For each droplet set where the average droplet volume is determined to be not acceptable, an existing droplet dispensing parameter is changed to a new droplet dispensing parameter that will cause the average droplet volume for that droplet set to change. Once the new droplet dispensing parameters have been selected, a burst curve is generated that will cause the new droplet dispensing parameter for each droplet set to be used if a subsequent plurality of droplet sets are dispensed.

DETAILED DESCRIPTION OF THE INVENTION

The present invention comprises a method for calibrating an acoustic liquid dispensing apparatus (such as the apparatus 10 shown in FIG. 1) to dispense droplets having volumes that are within a predetermined range.

Figure 3:
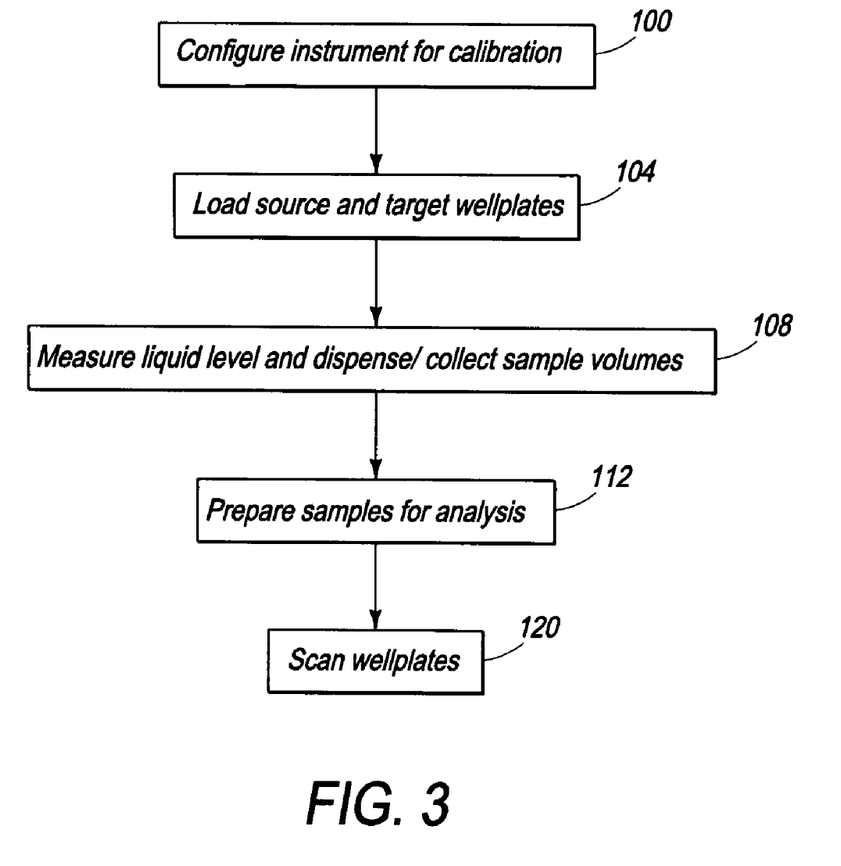
FIG. 3 is a flow chart according to the present invention.

The method of the present invention can be conceptually divided into two parts: sample preparation and data processing. The sample preparation part of the method is illustrated in FIG. 3. In step 100 of FIG. 3, an acoustic liquid dispensing apparatus (such as the apparatus 10 shown in FIG. 1) is configured to perform the calibration procedure. In a preferred embodiment, step 100 includes operations such as confirming the configurations of the source wellplate 44 and the target wellplate 70 by entering this information into a calibration program running on a computer, such as the computer 18. This involves specifying the number of wells in the wellplates, as well as the row and column configurations of the wells, so that the apparatus 10 can dispense droplets from and to specific wells on the wellplates 44 and 70, respectively. Additionally, the identity of the specific wells 46 to dispense from (usually specified by well numbers) and the identity of the specific wells 74 to dispense to, are specified.

Another parameter that is specified in a preferred embodiment of step 100 is the fluid and unit volume. This means that a desired volume for the droplets 60 is specified in certain units (e.g. droplets having a volume of one hundred picoliters each). The number of droplets to be dispensed is also specified. Another parameter that may be specified in a preferred embodiment of step 100 is to select certain calibration parameters from a database stored on the computer 18. For example, if the source liquid to be dispensed in the calibration operation is similar to a source fluid dispensed previously, then the calibration parameters from the earlier dispensing process can be selected as the starting point for the present calibration procedure. These parameters may include parameters such as the chemical name and/or composition of the source liquid and the burst curve (explained in FIG. 6) that will be used as the initial burst curve for dispensing droplets. Additional information that may be included is the energy required to dispense droplets of a certain volume from a well having a certain liquid level, the speed of sound in the fluid being dispensed, the wellplate type (i.e. the number of wells in the wellplates 44 and 70) and an identification number for the acoustic emitter assembly 29.

Part of step 100 also includes preparing the source wellplate (e.g. the source fluid containment structure 44) for the dispensing of droplets during the calibration process. This is done by filling a plurality of the wells 46 with a solution comprised of the source liquid 40 and a homogeneously mixed indicator, such as a fluorescent chemical like fluorescein. Preferably, several (e.g. 1-5) of the wells 46 are filled with a small volume of the solution. The actual volume of the solution used varies depending on factors such as the type of source wellplate being used (i.e. on the size of the wells 46), but typical volumes are in the range of one microliter ($\mu$L) to 20 $\mu$L per well. By way of example, a wellplate having 384 wells may use 18 $\mu$L of solution per well, while a 1536 well wellplate uses 6 $\mu$L per well, and a 3456 well wellplate uses one $\mu$L per well. In step 104 of FIG. 3, the source well plate 44 and the target wellplate 70 are positioned in the apparatus 10 so that dispensing from and to the wellplates 44 and 70 can begin. In a preferred embodiment, the source liquid 40 will have been added to the wells 46 from which dispensing will occur before step 104 occurs (e.g. in step 100 described above).

Figure 4:
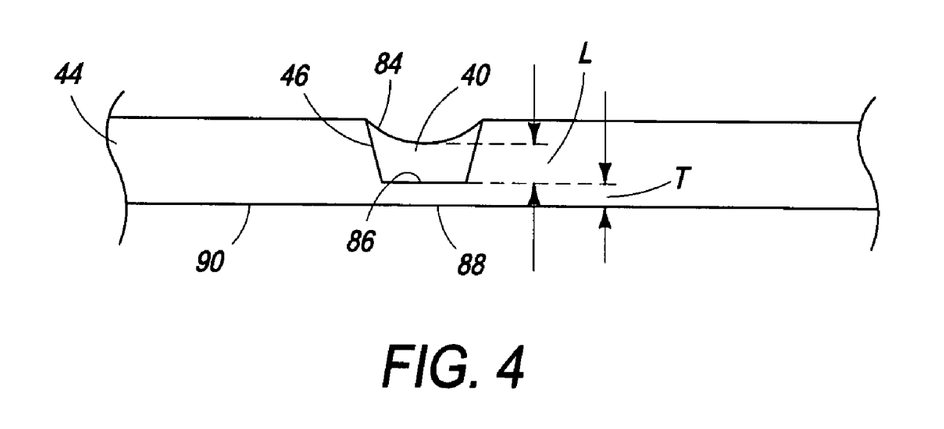
FIG. 4 is a cross sectional view of a well in a wellplate.

In step 108, two functions are performed by the acoustic liquid dispensing apparatus 10. First, the apparatus 10 measures the liquid level in the well or wells from which the droplets 60 are to be dispensed to yield a first liquid level, and the first liquid level is stored in the computer 10. The preferred technique for measuring liquid level is explained later. FIG. 4 illustrates that the liquid level "L" of the source liquid 40 in the source well 46 is the height of the free surface of the liquid 40 above the bottom of the well 46. Generally, L is the distance between the lowest part of the meniscus 84 of the liquid 40, and a well bottom surface 86 of the well 46 that is in contact with the liquid 40. However, other reference points could be used as the liquid level. FIG. 4 also illustrates that the wellplate 44 has a thickness "T" underneath the well bottom surface 86. The wellplate 44 has a wellplate bottom surface 88. A reference point 90 is a point on the wellplate bottom surface 88 that is not underneath the well 46.

Second, after the first liquid level in the well 46 has been measured, the apparatus 10 dispenses a first set of droplets comprised of a specified number of droplets having a specified target volume from the well 46 into the specified target well 74 to yield a first target well 74, all according to the instructions that were entered in step 100. In an exemplary embodiment, approximately eight to twelve droplets are dispensed into a single target well 74, yielding a total volume in that well 74 of approximately ten to twenty nanoliters (nL), before the backfilling described in step 112 below takes place. Hence, in this embodiment, each of the droplets 60 has a volume in the range of 0.8 nL to 2.5 nL. In other embodiments, other droplet volumes may be used. For example, each of the droplets 60 may have a volume in a range of 0.01 nL to 10 nL, 0.1 nL (100 picoliters) to 100 nL, or 10 nL to 1000 nL. Of course, other total well volumes and/or other numbers of droplets can also be used.

After the first set of droplets has been dispensed, the liquid level in the in the well 46 from which the first set of droplets were dispensed is measured again to yield a second liquid level, and the second liquid level is stored in the computer 10. After the second liquid level in the well 46 has been measured, the apparatus 10 dispenses a second set of droplets 60 comprised of a specified number of droplets having a specified target volume from the well 46 into an empty (i.e. clean and dry) single target well 74, referred to as the second target well 74.

After the second set of droplets 60 has been dispensed, the liquid level in the well 46 from which the second set of droplets was dispensed is measured again to yield a third liquid level, and the third liquid level is stored in the computer 10. After the third liquid level in the well 46 has been measured, the apparatus 10 dispenses a third set of droplets 60 from the well 46 into an empty target well 74, to yield a third target well. The process of measuring a new liquid level in the well 46 and dispensing another set of droplets 60 from the well 46 into an empty target well 74 is repeated as many times as is desired, or until the well 46 is nearly dry. In a preferred embodiment, droplets are dispensed into 300-500 target wells, depending on configuration of target well plate, with each target well receiving an 8-12 droplet fill.

In step 112, the target wellplate 70 is prepared for analysis. In a preferred procedure, the target wellplate 70 is removed from the apparatus 10 and the wells 74 into which the droplets of source liquid (plus indicator, such as a fluorescent dye) were dispensed (i.e. the 300-500 target wells) are backfilled with a known volume of a liquid that does not contain something that would interfere with the detection of the indicator or the source fluid. The volume of the liquid used for backfilling (the backfill liquid) varies depending on factors such as the type of target wellplate being used (i.e. on the size of the wells 74), but typical backfill volumes are in the range of 2-40 μL. By way of example, a target wellplate 70 having 384 wells 74 may use 40 μL of backfill liquid per well, while a 1536 well wellplate uses 6 μL per well, and a 3456 well wellplate uses 2 μL per well. The backfill liquid could be the source liquid without the indicator, or some other liquid like an organic solvent or aqueous buffer. Preferably, the backfill liquid should be chosen such that it actually enhances and stabilizes the indicator of the source liquid, but does not add any additional noise that would interfere with the detection of the indicator in the source liquid. The purpose is to create a known volume of liquid in each of the wells 74 where all of the indicating signal detected in those wells comes only from the droplets dispensed into those wells in step 108.

A selected number of wells in the wellplate 70 are used as calibration wells. The calibration wells are prepared by adding (e.g. by pipette) a calibration liquid containing a known concentration of the same indicator used in the source liquid to several wells in the wellplate 70. Furthermore, the calibration liquid would be the same liquid that was used to backfill the target wells, and the indicator is identical to the indicator used with the source liquid. Preferably, the indicator used in preparing the calibration liquid comes from the same stock solution that was used to prepare the source liquid. Furthermore, the calibration wells in the wellplate should contain a range of concentrations of the indicator. In an exemplary embodiment, the indicator is a fluorescent dye (e.g. fluorescein), and a three-point calibration is used with the concentrations of fluorescent dye in three separate wells 74 being one micromolar (μM), 10 μM and 100 μM. Of course other numbers of calibration points and/or other concentrations could be used. The target wellplate 70 is then centrifuged (e.g. at 2000-4000 rpm) to remove any bubbles that may have formed within the target wells.

In step 120, the target wellplate 70 is placed in a scanner that reads the quantitative amount of the indicator in each target well. In the preferred embodiment, the indicator is a fluorescent dye (e.g. fluorescein) and the scanner is reading the emission intensity of photons emanating from the fluorescein. A commercially available nanoplate reader (such as an Aurora tcPR) can be used to measure the indicator levels (e.g. as voltage) from each of the wells 74, including the calibration wells, and the results are stored in the computer 18. In the preferred embodiment, the indicator levels of the calibration wells and the sample wells of the target wellplate are measured during the same wellplate measurement (i.e. the calibration wells are on the same wellplate as the sample target wells).

The preferred technique for measuring liquid level (used in step 108) is to use the piezoelectric crystal in the acoustic wave emitter 14 to detect the reflection of the acoustic beam that is generated when the acoustic beam strikes the surface of the source liquid 40 (i.e. the meniscus 84 shown in FIG. 4). U.S. Pat. No. 6,596,239, which is incorporated herein by reference, illustrates representative hardware configurations for measuring liquid level. In the preferred embodiment of the present invention, a pulse or wave of acoustic energy is generated by a single piezoelectric crystal, such as the acoustic wave emitter 14. When the acoustic pulse strikes the meniscus 84, a meniscus reflected wave is generated. The meniscus reflected wave travels back to the acoustic wave emitter 14 where it is detected. Since the acoustic pulse will generate a reflected wave whenever it passes through a boundary between two materials of different acoustic impedance, reflected waves are also generated when the acoustic pulse passes through the wellplate bottom surface 88 (the wellplate reflected wave) and when it passes through the well bottom surface 86 (the well reflected wave). The time between when the acoustic pulse is generated and when the meniscus reflected wave is detected is designated as t1. Similarly, the time between when the acoustic pulse is generated and when the well reflected wave is detected is designated as t2. The liquid level (LL) is calculated using a calculation such as $LL = v*(t1-t2)/2$, where v is the speed of sound in the liquid 40.

In practice, sometimes the thickness T (shown in FIG. 4) may be so small that it is difficult to distinguish the well reflected wave from the wellplate reflected wave because these two reflected waves are too close together in time. One solution to this problem is to derive t2 by detecting the time of the wellplate reflected wave and adding the time it takes for the acoustic wave to travel through the material that forms the bottom of the well. This requires knowing the thickness of the well bottom (i.e. the thickness T in FIG. 4), and the associated speed of sound. These are values that can be obtained from the manufacturer of the wellplate.

In the equation given above for determining the liquid level LL, the speed of sound (v) in the liquid 40 must be known. There are a number of ways of learning v. For many known fluids, the speed of sound has been established. The value for v can be looked up in a reference manual and entered into the software by the user (e.g. in step 100 of FIG. 3).

Alternatively, the speed of sound can also be measured directly and the result entered into the software. The basic measurement technique is to have the acoustic wave travel through a known distance where that distance contains only the fluid of interest (e.g. the liquid 40). The speed of sound is then calculated by dividing the known distance by the measured time. The known distance can be established by using a special well with a calibrated height. The well is overfilled with the fluid and a "cap" is placed across the top of the well which will force out the excess fluid and assure that the well is completely filled with the fluid. By measuring the time difference of the echo from the bottom of the well and the echo from the top of the well (i.e. from the cap), the time to travel through the fluid is established. In other embodiments, other methods for determining the speed of sound and/or the liquid level may be utilized.

Figure 5:
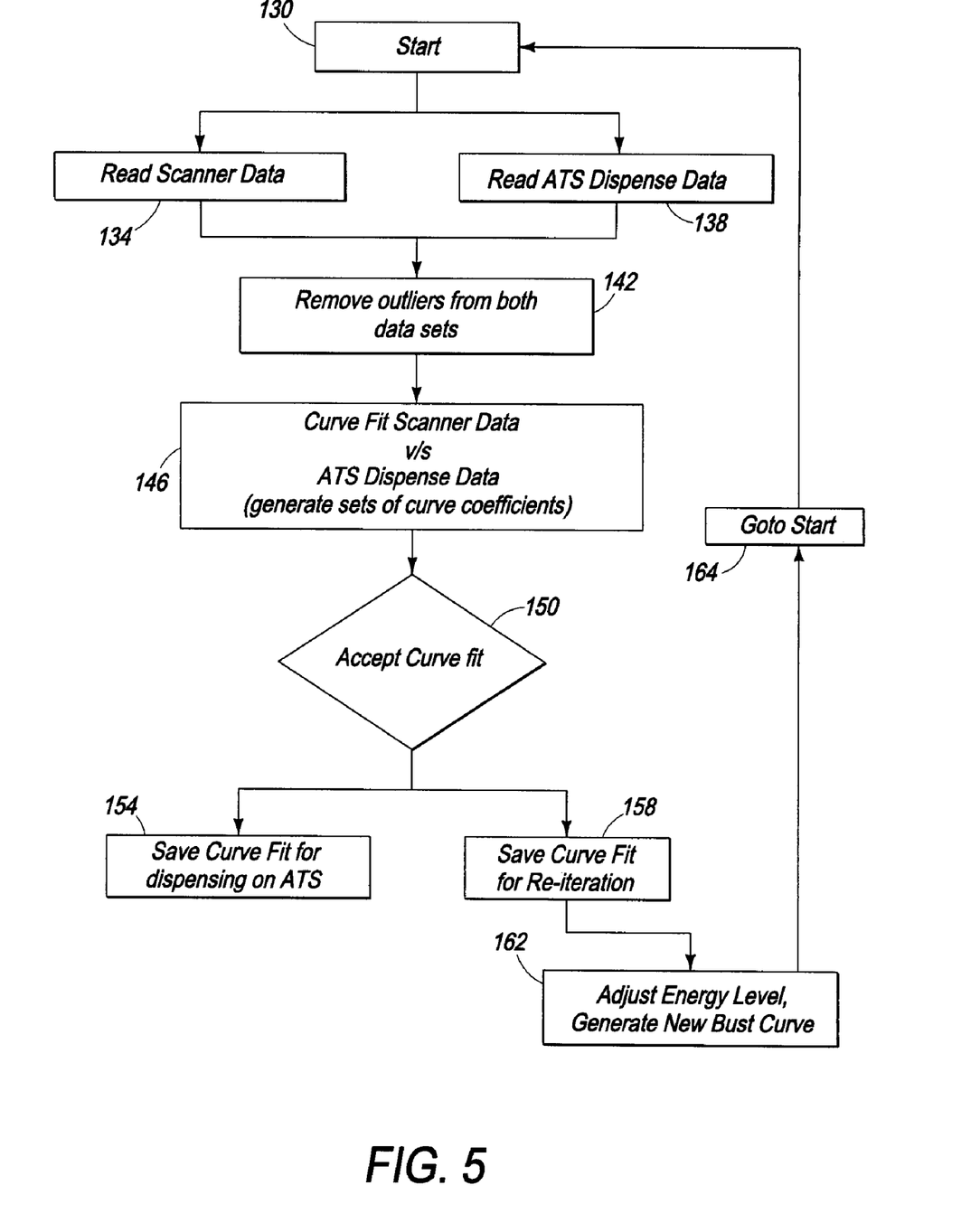
FIG. 5 is a flow chart according to the present invention.

FIG. 5 is a flow chart that illustrates the steps involved in the data processing part of the method for calibrating the acoustic liquid dispensing apparatus. In step 130, the user begins the data processing procedure by selecting a scanner data file stored on the computer 18. The scanner data file includes the results from step 120 in which the calibration wellplate and the target wellplate 70 were scanned. The scanner data is read in step 134, meaning that a program running on the computer 18 fetches the source fluid chemical indicator measurements for each of the wells 74 and for each of the calibration wells. (Henceforth, the chemical indicator is assumed to be a fluorescent dye like fluorescein, so the indicator measurements are fluorescence measurements, typically reported in millivolts, and are also referred to as npr data for nano plate reader data). In step 138, the dispense data is read, meaning that a program running on the computer 18 fetches the dispense data generated in step 108. The dispense data includes information such as the number of droplets dispensed into each target well 74, the liquid level in the source well 46 from which the droplets were dispensed, any errors that occurred during droplet dispensing (i.e. machine errors) and other information.

In step 142, data that lies outside of predetermined criteria (e.g. extraneous data criteria) is removed from the scanner data set and from the dispense data set. For example, if the number of droplets reading is zero, then the scanner data related to the associated target well 74 is deleted. Similarly, if the scanner data is outside of a predetermined range (either low or high), that data is deleted (as is the corresponding dispense data).

Figure 6:
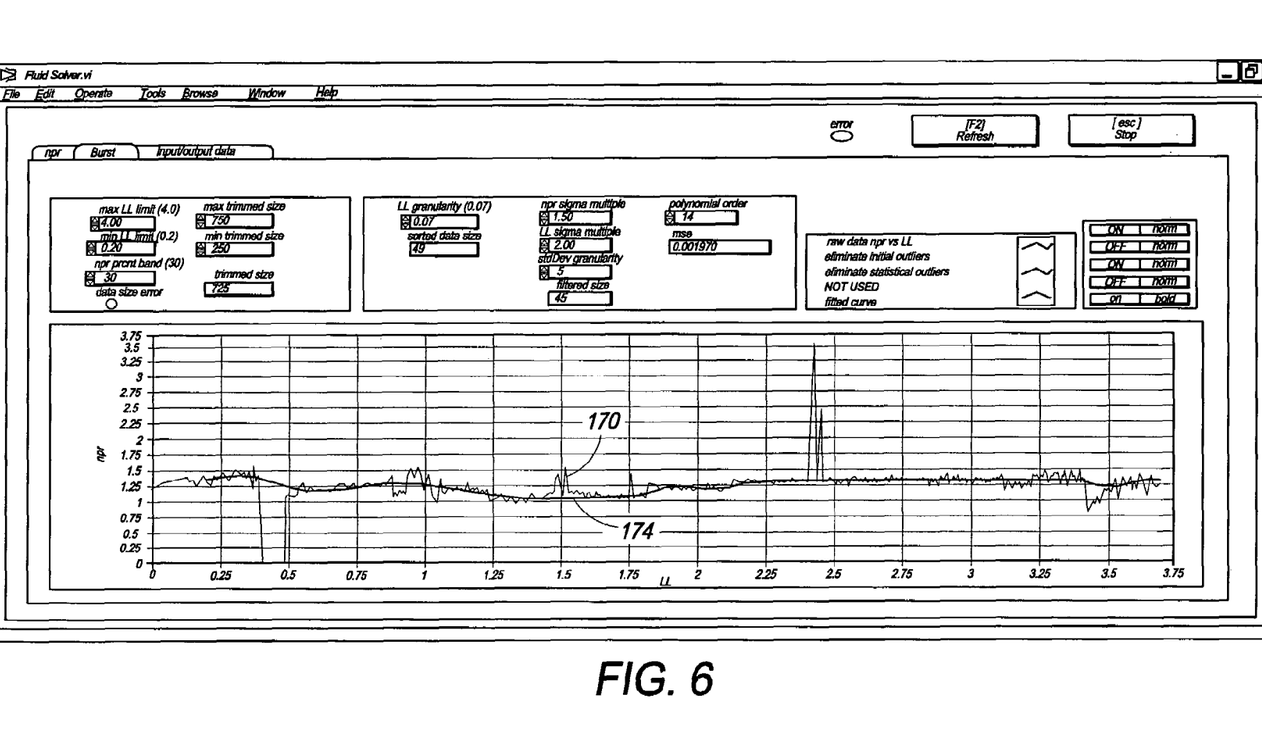
FIG. 6 is a scanner output curve according to the present invention.

In step 146, parts of the scanner data and dispense data are processed and electronically graphed. In a preferred embodiment, the raw output from the scanner (npr) for the target wells (i.e. the 300-500 target wells) is plotted against the liquid levels (LL) in the source well 46 from which the droplets were dispensed by the calibration program running on the computer 18. This data (npr v. LL) is then processed (smoothed) by averaging the npr data into a predetermined number of liquid level groups. For example, in step 108, if the liquid level in the source well 46 was measured at thirty-six discrete levels, then there would be thirty-six LL groups. The fluorescence (indicator) readings (npr data) for all of the target wells 74 into which droplets were dispensed between two LL groups would be averaged and used as the npr reading at the higher (i.e. first) liquid level reading (or the average liquid level reading of the two LL groups). So, for example, the npr readings for ten wells 74 might be averaged and used as the npr reading for a liquid level of 1.5 milliliters (mL). FIG. 6 illustrates an exemplary electronic graph of the npr versus LL data. A curve 170 illustrates the raw npr versus LL data, and a curve 174 illustrates the smoothed npr versus LL data.

Once the smoothed npr versus LL data has been generated (i.e. curve 174), the data are examined for readings that are unacceptably high or low (i.e. out-of-spec point). In a preferred embodiment, out-of-spec points are determined by calculating the actual volume of the droplets dispensed at a given LL value. In alternate embodiments, out-of-spec points could be determined using other techniques, such as by calculating an expected npr value. An expected npr value for the desired droplet volume would be calculated assuming that the desired droplet volume was actually dispensed at a given LL value; that is, by determining what npr value should be obtained based upon the readings of the three-point calibration standards.

In the preferred embodiment, the actual droplet volume (dV) is calculated by using the npr data from the three-point calibration curve prepared in step 112. In general, the unknown concentration of fluorescein in the target wells 74 is extrapolated from the three-point calibration curve by comparing the npr value for the target well (or wells) to the npr values on the three-point calibration curve. In the preferred embodiment, it is the npr values that correspond to each of the discrete liquid level groups (thirty-six groups in the example discussed above) that are of interest. As mentioned previously, the npr value associated with each discrete liquid level group may be obtained by averaging the npr data obtained within each of the discrete liquid level groups.

The npr value at each of the discrete liquid level values is compared to the three-point calibration curve. This yields the extrapolated concentration of fluorescein ([Fex]) at each of the discrete liquid level values. The volume of each droplet (dV) corresponding to each discrete liquid level value is calculated by using the concentration of fluorescein in the sample target wells ([Fex]); the known concentration of fluorescein ([Fknown]) from step 100; the known volume (V) of liquid that was added to the target wells 74 during the backfilling part of step 112; and the number of droplets (nD) dispensed into each sample target well (as specified in step 100). The volume of each droplet (dV) is calculated by the computer 18 using a formula such as:

$$dV=[Fex]*V/([Fknown]*(nD)).$$

Of course, since the npr values that correspond to each of the discrete liquid level groups are used in the preferred embodiment, the value dV is actually an average or representative volume of the individual droplet volumes that were dispensed for a particular liquid level value. If the npr value for a single target well 74 is used to extrapolate [Fex], then dV would correspond to the average droplet volumes that were dispensed into the single well.

In a preferred embodiment, once the droplet volume is known, out-of-spec points are determined by calculating the difference between the observed droplet volume (dV) and the desired droplet volume that was specified in step 100 before droplet dispensing began. The difference may be expressed as a coefficient of variation (CV), a standard deviation (SD) and/or some other parameter. If the difference is unacceptably large, then a droplet dispensing parameter can be changed to change the volume of droplets dispensed at that liquid level. The droplet dispensing parameter is changed by changing a coefficient in a burst curve, such as the burst curve 190 illustrated in FIG. 7. In the preferred embodiment, an initial burst curve was selected in step 100 (FIG. 3) to use for the initial cycle of droplet dispensing.

Figure 7:
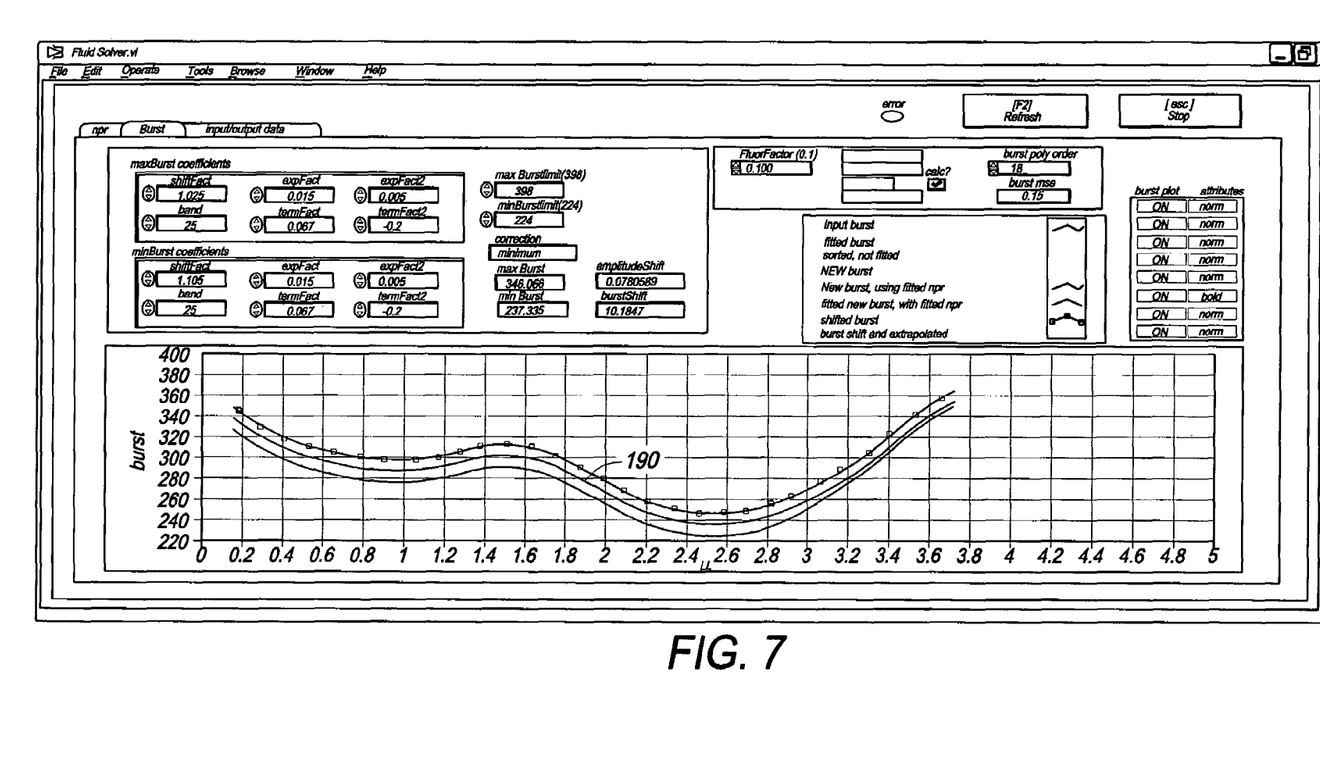
FIG. 7 is a burst curve according to the present invention.

In the burst curve 190, a burst value (burst) is electronically plotted versus liquid level (LL). The burst value represents the energy of the acoustic burst generated by the acoustic wave emitter 14 (FIG. 1) to dispense the droplets 60. The shape of the burst curve 190 is mathematically modeled using standard curve fitting technique, which results in the shape of the burst curve 190 being described by a plurality of curve coefficients (coefficients). By changing the coefficients, the shape of the curve 190 changes, and hence the droplet dispensing parameter (or parameters) is changed. Preferably, the droplet dispensing parameter controls the time duration of the acoustic burst used to dispense the droplet, or the amplitude of the acoustic burst. In general, the burst curve is used to control the droplet dispensing parameter, and the burst curve comprises a data set that correlates a burst setting to liquid level.

In step 150 of FIG. 5, after the difference between the observed droplet volume (dV) and the desired droplet volume has been calculated, a decision must be made (e.g. by the person operating the apparatus 10) as to whether the difference in droplet size is acceptable or not. If the difference is acceptable, then in step 154 the burst curve 190 is accepted and stored by the calibration program for future use.

If the difference between the observed droplet volume (dV) and the desired droplet volume is unacceptable, then in step 158 the burst curve 190 is saved for reiteration and a reiteration process is initiated. In the reiteration process, the points on the npr v. LL graph (i.e. curve 174 in FIG. 6) are examined. In step 162, where the npr data is high is higher the acceptable, the setting for the burst energy at that LL setting is reduced. Where the npr data is low, the setting for the burst energy at that LL setting is increased. These new burst settings are stored and a new (second) burst curve 190 is modeled using curve fitting techniques. The new burst curve is saved (e.g. in step 100), and in step 164, the calibration procedure outlined in FIGS. 3 and 5 is repeated. This process is repeated until acceptable coefficients are obtained in step 150.

The curve fitting technique used to model the burst curve 190 yields a plurality of curve coefficients that define the curve. In representative cases, the curve fitting process can involve multi-order polynomials (e.g. 1-20 order polynomials, meaning 1-20 coefficients). The curve fitting functions from commercial software programs, such as Microsoft's Excel program, MathWorks' MATLAB program, Wolfram's Mathematica program or National Instruments' Lab View program, can be used for generating (curve fitting) the burst curve 190.

The method for calibrating the droplet dispensing apparatus 10 comprises using acoustic energy to dispense a plurality of droplet sets of the liquid 40 from the source container 46 into a plurality of target containers 74, with each droplet set being comprised of one or more individual droplets 60 of the liquid, and with a liquid level of the liquid in the source container being measured before or after each of the droplet sets are dispensed. Step 108 in FIG. 3 discusses this procedure. It should be noted that in the preferred embodiment, the liquid level was measured before each of the droplet sets was dispensed. However, the liquid level could be measured after each of the droplet sets was dispensed. Next, the average droplet volume for the individual droplets in each of the droplet sets is calculated. Typically, this is done by detecting the presence of an indicator, such as a fluorescent chemical, as was explained previously in relation to step 146 of FIG. 5. In other embodiments, the volume of dispensed droplet sets may be determined by techniques such as measuring the change in liquid levels in the source wells, or by using visual techniques to measure physical aspects and parameters of the droplets 60 of the dispensed droplet sets.

Once the average droplet volume has been calculated, it is determined if the average droplet volume for each droplet set is acceptable or not acceptable, for example as was explained previously in relation to step 150 of FIG. 5. For each droplet set where the average droplet volume is determined to be not acceptable, an existing droplet dispensing parameter is changed to a new droplet dispensing parameter that will cause the average droplet volume for that droplet set to change, as was explained previously in relation to step 162 of FIG. 5. Once the new droplet dispensing parameters have been selected, a burst curve (such as curve 190 shown in FIG. 7) is generated that will cause the new droplet dispensing parameter for each droplet set to be used if a subsequent plurality of droplet sets are dispensed. Typically, the new burst curve would be used to dispense the same liquid 40, from the same type of source well 46 as was used to generate the burst curve.

The burst curve 190 allows the droplet dispensing apparatus 10 to dispense droplets having a uniform volume even as the liquid level in the source container 46 changes. This is because the shape of the burst curve causes the droplet dispensing parameter to change as the liquid level changes. The ability to generate the burst curve 190 (also called calibration curves) yields many other operational advantages to the droplet dispensing apparatus 10. First, a plurality of burst curves can be stored in a database associated with the computer 18. For example, two or burst curves or ten or more burst curves can be stored in the database. This database can be located on either a local or a network drive. The stored burst curves mean that the droplet dispensing apparatus 10 doesn't have to be recalibrated every time the source liquid is changed. The stored burst curves also mean that several different source liquids can be loaded in different wells on the same wellplate, and an appropriate burst curve can be used in real-time to control the dispensing of droplets of the different source liquids.

Additionally, an easy to use graphical user interface can be used to manage the stored burst (calibration) curves. This allows the user to select the calibration curve to be used in the next dispense operation, delete a calibration curve, edit a saved calibration curve, manually add a calibration curve to the database, and plot and view calibration curves. Additionally, the user can specify configurations such as selecting the source and/or target wellplate configurations to use before dispensing the one or more droplets, or selecting a target region to dispense the one or more droplets to before dispensing the one or more droplets.

Typically, each of the calibration curves stored in the database is associated with a transporter identification that identifies acoustic emitter assembly 29 (including the acoustic emitter 14 and lens 28) used for the dispense operation; the source wellplate type and the speed of sound in the source liquid. All of these factors increase the throughput of dispensing operations by allowing an appropriate calibration curve to be selected.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. A method for calibrating a droplet dispensing apparatus comprising:
   a) using acoustic energy to dispense a first plurality of droplets of a liquid from a source container into one or more first target containers, the liquid including a known concentration of an indicator, and with a first liquid level of the liquid in the source container being known before the first plurality of droplets are dispensed;
   b) determining a second liquid level of the liquid in the source container after the first plurality of droplets are dispensed;
   c) using acoustic energy to dispense a second plurality of droplets of the liquid from the source container into one or more second target containers;
   d) measuring an indicator parameter in one or more of the target containers, the indicator parameter being associated with the indicator and giving an indication of a total volume of the droplets collected in each individual target container for which the indicator parameter is measured;

e) generating a data set that correlates the indicator parameter for each target container versus the liquid level of the liquid in the source container from which the droplets were dispensed; and f) evaluating the data set for one or more out-of-spec points, the one or more out-of-spec points indicating a liquid level where the volume of the plurality of droplets at that liquid level have a value that is outside of an acceptable range.

2. The method of claim 1 further comprising:

g) using the presence or absence of one or more out-of-spec points to decide if the acoustic energy being used to dispense the droplets is acceptable.

3. The method of claim 1 further comprising:

g) if one or more out-of-spec points are found, changing a droplet dispensing parameter that will alter the volume of the droplets dispensed from the source container at the liquid level associated with the out-of-spec points if additional droplets are dispensed.

4. The method of claim 3 wherein the droplet dispensing parameter controls the time duration of an acoustic burst associated with the acoustic energy or the amplitude of the acoustic burst.

5. The method of claim 3 further comprising:

generating a burst curve to control the droplet dispensing parameter, the burst curve comprising a data set that correlates a burst setting to liquid level.

6. The method of claim 5 wherein the burst curve is defined by a one to twenty order polynomial.

7. The method of claim 1 further comprising:

after step "c," using acoustic energy to dispense one or more additional plurality of droplets of the liquid from the source container into one or more additional sets of target containers with a new liquid level of the liquid in the source container being determined before each additional plurality of droplets is dispensed.

8. The method of claim 7 further comprising:

generating a final burst curve to control the dispensing parameter, the final burst curve comprising a data set that correlates a burst setting to liquid level; and storing the final burst curve so that the final burst curve can be used to control the dispensing of one or more droplets in the future.

9. The method of claim 1 wherein the indicator comprises a fluorescent material and the indicator parameter is fluorescence.

10. The method of claim 1 wherein the first plurality of droplets and the second plurality of droplets have a droplet volume in the range of approximately one hundred picoliters to one hundred nanoliters.

11. The method of claim 1 wherein the first plurality of droplets and the second plurality of droplets have a droplet volume in the range of approximately ten nanoliters to one thousand nanoliters.

* * * * *